(12) United States Patent
Matthias et al.

(10) Patent No.: US 9,155,842 B2
(45) Date of Patent: Oct. 13, 2015

(54) MEDICATION DELIVERY DEVICE AND METHOD OF ASSEMBLING A MEDICATION DELIVERY DEVICE

(75) Inventors: Claudia Matthias, Frankfurt am Main (DE); Michael Helmer, Frankfurt am Main (DE); Kerstine Hemmann, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 638 days.

(21) Appl. No.: 13/002,976

(22) PCT Filed: Jun. 30, 2009

(86) PCT No.: PCT/EP2009/004691
§ 371 (c)(1),
(2), (4) Date: Apr. 8, 2011

(87) PCT Pub. No.: WO2010/003569
PCT Pub. Date: Jan. 14, 2010

(65) Prior Publication Data
US 2011/0276006 A1    Nov. 10, 2011

(30) Foreign Application Priority Data

Jul. 9, 2008  (EP) .................................... 08012371

(51) Int. Cl.
*A61M 5/315* (2006.01)
*A61M 5/31* (2006.01)

(52) U.S. Cl.
CPC ....... *A61M 5/31525* (2013.01); *A61M 5/31555* (2013.01); *A61M 5/3155* (2013.01); *A61M 2005/3125* (2013.01); *A61M 2005/3126* (2013.01); *A61M 2205/583* (2013.01); *A61M 2205/585* (2013.01); *A61M 2205/586* (2013.01); *Y10T 29/49826* (2015.01)

(58) Field of Classification Search
CPC ............. A61M 2005/3125; A61M 2005/3126; A61M 2205/58; A61M 2205/583; A61M 2205/585; A61M 5/31525; A61M 5/31555; A61M 5/3155; A61M 2205/586
USPC ........................... 604/181, 187; 359/440–442
See application file for complete search history.

(56) References Cited

U.S. PATENT DOCUMENTS 2,382,771 A * 8/1945 Bowers .......................... 604/300
4,040,419 A * 8/1977 Goldman ....................... 604/187
(Continued)

FOREIGN PATENT DOCUMENTS

WO           00/41754 A        7/2000

OTHER PUBLICATIONS

Form PCT/IB/326 (Jan. 2004) (PCT/EP2009/004691).

*Primary Examiner* — Aarti B Berdichevsky
*Assistant Examiner* — Laura Schell
(74) *Attorney, Agent, or Firm* — McDonnell Boehnen Hulbert & Berghoff LLP

(57) ABSTRACT

A medication delivery device (1) comprises an indicator element (3) having indications (300) and a magnifying device located over an indication position (32). The magnifying device (4) comprises an optical system (5) with a magnifying lens (43) wherein the optical system (5) is constructed such that the optical path length between the indication position (32) and the magnifying lens (43) is enlarged. As an example, the medication delivery device (1) is a pen-type device, wherein a dose dial element (30) having a dosage scale (31) is disposed. The magnifying device (4) generates a magnified image of the dosage scale (31) so that the size of the selected dose (33) of the medical product is visible through a window (41). A method for assembling the medication delivery device (1) includes providing a medication delivery device (1) having a receptacle and mounting an element of the magnifying device (4) at the receptacle.

11 Claims, 3 Drawing Sheets

(56) References Cited

U.S. PATENT DOCUMENTS

| | | | |
|---|---|---|---|
| 4,208,588 A * | 6/1980 | Rudin | 250/496.1 |
| 5,498,243 A * | 3/1996 | Vallelunga et al. | 604/197 |
| 6,001,082 A * | 12/1999 | Dair et al. | 604/207 |
| 6,932,242 B2 * | 8/2005 | Gerlach et al. | 222/113 |
| 6,936,032 B1 | 8/2005 | Bush, Jr. et al. | |

\* cited by examiner

MEDICATION DELIVERY DEVICE AND METHOD OF ASSEMBLING A MEDICATION DELIVERY DEVICE

The present invention relates to a medication delivery device for the administration of a dose of a drug, for example insulin, where different dosage sizes can be set. Here, it is important that the size of the selected dose is clearly visible for the user.

WO 2004/078239 A1 discloses a medication delivery device with a drive mechanism for setting and injecting a dose of a medical product. The medication delivery device comprises a housing wherein a dose dial sleeve is disposed. The dose dial sleeve comprises a dosage scale, which indicates a selective dose of the medical product. A dose can be set by rotating the dose dial sleeve with respect to the housing. The selected dose can be injected by the movement of a drive sleeve in a longitudinal direction of the medication delivery device.

U.S. Pat. No. 6,001,082 discloses a medication delivery pen having a magnifier for magnifying dosage numerals.

It is an aim of the present invention to provide a magnifying device for a medication delivery device so that an indication is clearly visible for the user.

For this aim, a medication delivery device comprises an indicator element having indications and a magnifying device which is located over an indication position of the indicator element. The magnifying device comprises an optical system with a magnifying lens, wherein the optical system is constructed such that the optical path length between the indication position of the indicator element and the magnifying lens is enlarged.

An enlargement of the optical path length means that the optical path length for light beams propagating along an optical path from the indication position of the indicator element to the magnifying lens is larger than the direct geometrical path length between the indication position and the magnifying lens. As a result, the incidence angles of the light beams on the magnifying lens are modified such that an optimal magnification factor can be achieved. Thereby, the magnifying device and, in particular, the optical system generates a magnified image of the indication located at the indication position of the indicator element. Preferably, the magnified image is large enough so that it can conveniently be viewed by a user.

The indications may be markings, symbols, characters, numerals or the like and are, e.g., printed on the surface of the indicator element.

In a preferred embodiment, the medication delivery device comprises a housing, wherein a dose dial element having a dosage scale is disposed. The magnifying device is located over an indication position of the dosage scale where the size of the selected dose is indicated. Thus, the indication position is a part of the dosage scale which is fixed relative to the housing of the medication delivery device, but moves relative to the dosage scale.

By an enlargement of the optical path length, the lens can be positioned close to the housing of the medication delivery device while a sufficient magnification factor can be achieved. If the lens was positioned in a distance from the housing which equals the geometrical distance, the thickness of the medication delivery device would be increased to a higher extent.

This can be of importance, e.g., if the indications indicate the size of a selected dose and if insulin pens with cartridges comprising different amounts of insulin units are delivered out, while the dimensions of the cartridges and the pen shall remain the same. As an example, cartridges with 80 insulin units and cartridges with 240 insulin units are available. In the first case, the selected dose can be indicated by dosage numerals with up to 2 digits, while in the second case, dosage numerals with up to 3 digits are required. If the sizes of the cartridges are identical in both cases, the dosage numerals comprising 3 digits may have to be depicted in a smaller font size. Here, in order to achieve a convenient readability of the dosage size, the numerals are magnified by a magnifying lens.

In a preferred embodiment, the optical system comprises a mirror. Preferably, the mirror is suitable for reflecting light beams emitted from the indication position of the indicator element towards the magnifying lens.

As an example, the mirror may be formed by a reflecting surface of a casing or may be a separate element attached to a casing. In one embodiment, the mirror and the lens are integrally formed. As an example, they may be parts of a transparent element. Alternatively, the mirror may be located at an inner surface of a casing of the magnifying device and the lens may be a separate element which is positioned at a front end of the magnifying device.

In a preferred embodiment, the magnifying device comprises a window for making a magnified image of an indication of the indicator element visible from the outside.

This means that a magnified image of the part of the indication at the indication position can be viewed through the window. As an example, the window is an opening in the magnifying device. Preferably, the magnifying lens is located in the window.

In one embodiment, the indications comprise numerals or characters which are depicted in a mirror inverted manner.

By this way, the image of the numerals formed after the reflection of the light beams at a mirror is in the correct orientation so that it can be read from the outside.

Preferably, the window is inclined against the outer surface of the indicator element at its indication position.

Here, the outer surface of the indicator element is the surface, where the indications are depicted. Accordingly, a user's line of sight through the window is not frontally directed towards the indications at the indication position of the indicator element.

In one embodiment, the magnifying device is suitable for making a magnified image of an indication visible from the left hand side of the medication delivery device.

As an example, a window of the magnifying device is oriented to the left hand side of the medication delivery device. This embodiment is most convenient for a right-handed person. Usually, during injection, a right-handed person will hold the medication delivery device in his/her right hand and will look onto a side of the medication delivery device. The term "left hand side of the magnifying device" relates to such a line of sight. By the term "visible" it is meant that the indications are not only visible but also readable.

In an alternative embodiment, the magnifying device is oriented such that a magnified image of an indication is visible from a right hand side of the medication delivery device.

Here, preferably, a window of the magnifying device is oriented towards the right hand side of the medication delivery device. This embodiment is most suitable for a left-handed person. Usually, a left-handed person will hold the medication delivery device in his/her left hand and will look onto the right hand side of the medication delivery device.

Furthermore, a method of assembling the medication delivery device with a magnifying device is described. A medication delivery device with an indicator element having indications and a mountable element forming at least a part of the magnifying device are provided. The medication delivery device comprises a receptacle which is located over the indication position of the indicator element.

Preferably, the medication delivery device and the mountable element are delivered out as separate elements and the user or a pharmacist can mount the mountable element at the receptacle. Here, the user or pharmacist can optionally mount the mountable element such that a magnified image of the indication is visible from the left hand side or from the right hand side of the medication delivery device.

In one embodiment, a medication delivery device comprises two windows which may be openings in a casing located over an indication position of the indicator element. One of the windows is suitable for making a magnified image visible from the left hand side and the other one is suitable for making a magnified image visible from the right hand side of the medication delivery device. Preferably, the casing comprises a receptacle for an element of the optical system.

Furthermore, a mountable element comprising at least a part of the magnifying device is delivered out which can be inserted into the casing such that the magnified image is visible in a selected one of the windows. Preferably, also a masking element is delivered out, which is suitable for masking the non-used window.

In one embodiment, the mountable element of the magnifying device forms the magnifying lens.

In a further embodiment, the mountable element of the magnifying device forms the optical system.

As an example, the optical system comprises a transparent element, where the magnifying lens and the mirror are included, and which can be inserted in one of the windows.

In a further embodiment, the medication delivery device is delivered out with two windows and two complete optical systems such that the size of the selected dose is visible through both windows.

In these cases, a masking element can be delivered out for masking one of the windows. Thereby, a confusion of the user by the existence of two windows or even by the existence of two magnified images of an indication can be avoided.

In a further embodiment, a medication delivery device with a mountable magnifying device is delivered out.

In this embodiment, the medication delivery device has a receptacle for the magnifying device which is located over an indication position of the indicator element. Preferably, the user or the pharmacist can mount the magnifying device in a preferred orientation, such that the size of the selected dose is either visible from the left hand side or from the right hand side of the medication delivery device.

Preferably, in the embodiments, where an element of the magnifying device can be mounted in a preferred orientation, the indicator element comprises two indication positions. At one of the indication positions indications are depicted which may be viewed through a window oriented towards the left hand side of the medication delivery device and at the other indication position indications may be viewed through a window oriented towards the right hand side of the medication delivery device.

As an example, a dose dial element comprises two dosage scales, which have an offset towards a longitudinal direction of the medication delivery device. At each dosage scale an indication position is located.

The receptacle is located over the indication positions such that for each orientation of the magnifying device, the magnifying device is located over the appropriate indication position and a correct image of the indication is generated.

In a further preferred embodiment the magnifying device is mounted such that removal of the magnifying device from the rest of the medicament delivery device disables proper use, especially dose delivery, of the medicament delivery device.

Removal of the magnifying device will always leave a free opening in a body of the medicament delivery device through which indexes of the indexing means, for example an indexing sleeve, are visible. Due to the optical system, the information visible directly through this opening and the information which should be displayed in the magnifying device may be different. Also, a number of indexes may be visible through the opening, in which case it becomes unclear which of the indexes refers to the dose currently set. Removal of the magnifying device will therefore probably result in setting and injecting wrong doses. This may lead to severe physiological effects such as hypo- or hyperglycemia in case of an insulin delivery device.

Disablement of the use of the medicament delivery device after removal of the magnifying device therefore significantly increases the safety of the medicament delivery device, as a dose delivery will be completely impossible after removal of the magnifying device.

Preferably, the medicament delivery device comprises at least two body parts, e.g. half shells, wherein the magnifying device forms a connection means for the at least two body parts of the medicament delivery device.

In this embodiment, removal of the magnifying device results in a breach of the connection of the at least two body parts. Therefore, the body may fall apart or at least may not be able to properly transfer force along the load path. In both cases, however, a use of the medicament delivery device will be impossible.

As an alternative or additionally, the magnifying device preferably forms a support for parts of drive means of the medicament delivery device. Removal of the magnifying device will then either lead to an interrupt of the force flux so that the load path is incomplete and dose setting and/or delivery will be inhibited or to the loss of the connection between drive means and body. In that case, parts of the drive means or the whole drive means may fall out of the body.

As an alternative or additionally, the body may have at least one weakened area, e.g. a weak link, which is normally supported by the magnifying device and which is designed such that the body tears apart while removing the magnifying device. Therefore, the magnifying device may advantageously be provided with features to support or initiate tearing apart of the weakened area of the body. Such features may preferably be one or more protrusions or one or more hooks formed in or attached to the magnifying device. Also, a material connection between the magnifying device and the body in the area of the weakened part may be suitable.

In all of the three embodiments described before, a connection between the magnifying lens and the body and/or the drive means may be provided by laser welding or bonding.

Other features will become apparent from the following detailed description when considered in conjunction with the accompanying drawings.

Figure 1:
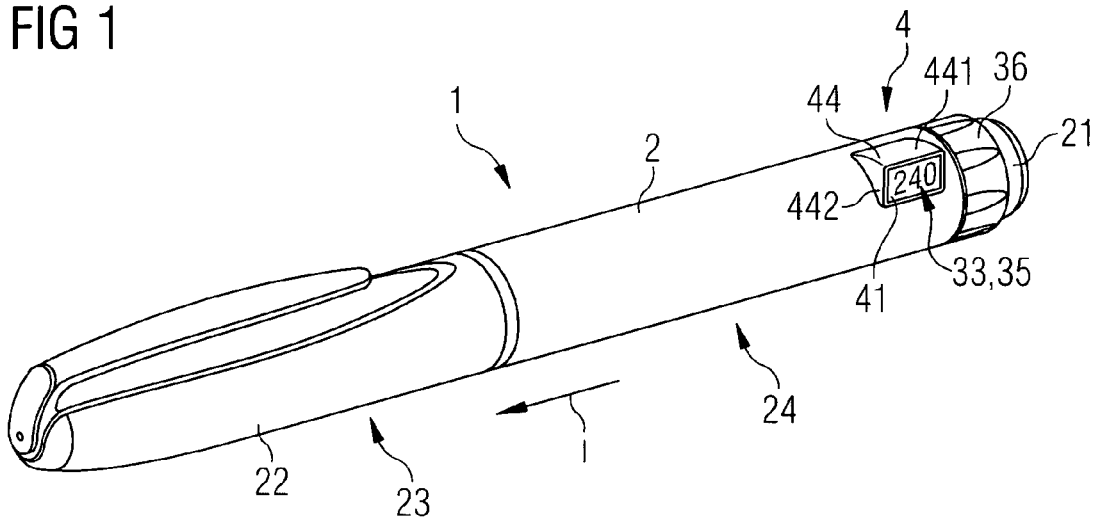
FIG. 1 is a perspective view of a medication delivery device comprising a magnifying device.

In FIG. 1, a pen-type medication delivery device 1 with a magnifying device 4 is shown. The medication delivery device 1 comprises a housing 2 with a front part 23, wherein a cartridge (not shown) containing a medical product is disposed. Through a needle unit (not shown) located at the front end of the medication delivery device 1, the medical product can be injected into a patient's skin. The front part 23 is covered by a cap 22 which is removed before the injection. In a rear part 24 of the housing 2, a dose dial element (not shown here) comprising a dosage scale is disposed.

For setting a dose, a user rotates the dose dial grip 36 which is connected to the dose dial element. Thereby, the dose dial element carries out a rotational and a translational movement in a direction opposite to the longitudinal direction l of the medication delivery device 1. The longitudinal direction l is defined as the direction from the dose dial grip 36 at the rear part 24 of the medication delivery device 1 towards the needle unit at the front end of the front part 23 of the medication delivery device 1. Such a pen-type medication delivery device 1 has a central axis running along the longitudinal direction l. By pressing onto a dispense button 21, the dose is injected. The user can view the size of the dialled dose 33 through a window 41 in a casing 44 of the magnifying device 4.

The casing 44 may be an integral part of the housing 2. Alternatively, the casing 44 may be a separate element which is attached to the housing 2.

The casing 44 of the magnifying device 4 has an upper part 441 which extends away from the housing 2 of the medication delivery device 1 and a lower part 442 which is adjacent to the housing 2 of the medication delivery device 1.

In this embodiment, the window 41 is suitable for making the size of the selected dose 33 visible from the left hand side of the medication delivery device 1, which is most convenient for a right-handed person. Usually, during injection, a right-handed person will hold the medication delivery device 1 in his/her right hand such that the longitudinal direction l of the medication delivery device 1 is oriented from the person's right-hand side to his/her left-hand side. The term "left hand side of the pen" relates to such a line of sight. By the term "visible" it is meant that the indications are not only visible but also readable. Here, the numerals occur in an upright, non-mirror inverted orientation. Thus, when the person looks onto the left-hand side of the medication delivery device 1, he can easily read the dialled dose through the window 41.

In another embodiment of the medication delivery device 1, the magnifying device 4 and the window 41, in particular, is oriented such that a left-handed person can easily read the selected dose 33 through the window 41. In this case, the window 41 is oriented towards the right hand side of the medication delivery device 1. Usually, a left-handed person will hold the medication delivery device 1 in his/her left hand and look onto the right hand side of the medication delivery device 1. When the window 41 is oriented towards the right hand side, the selected dose 33 is readable.

Figure 2:
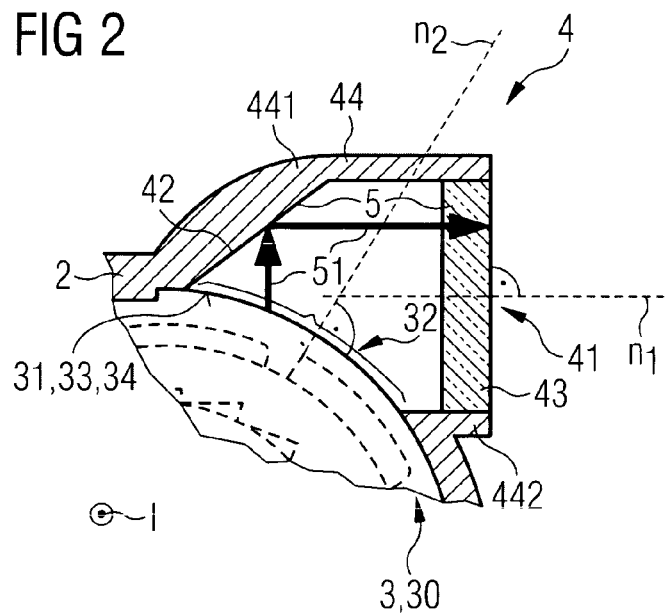
FIG. 2 is a cross-sectional view of the magnifying device of FIG. 1.

In FIG. 2, a cross-section of the magnifying device 4 according to FIG. 1 is shown. The magnifying device 4 is located over an indication position 32 of the dosage scale 31 in which the selected dose is indicated. The dosage scale 31 comprises mirror-inverted numerals which correspond to the size of the selected dose. Due to the fact that the dose dial element 30 has a limited outer surface, the mirror-inverted numerals of the dosage scale 31 may have font sizes which are too small so that they can conveniently be read by the user without a magnifying device 4. Preferably, the image has a font size of at least 3.5 mm.

When dialling a dose, the dose dial element 30 and therewith the dosage scale 31 carries out a rotational and a translational movement in a direction opposite to the longitudinal direction l of the medication delivery device 1. At an indication position 32 of the dosage scale 31, the part of the dosage scale 31 is present which indicates the selected dose.

The magnifying device 4 is located over the indication position 32 of the dosage scale 31. The magnifying device 4 comprises an optical system 5 and generates a magnified image of the part of the dosage scale 32 which indicates the selected dose. Thereby, the user can conveniently view the size of the selected dose 33 through the window 41. The optical system 5 comprises a magnifying lens 43 which is positioned in the window 41. Light beams 51 emerging from the part of the dosage scale 32 at the indication position 32 are reflected by a mirror 42 towards the lens 43. Thereby, the optical path length of light beams 51 propagating from the part of the dosage scale 31 at the indication position 32 towards the lens 43 is larger than the direct geometrical distance between the indication position 32 and the lens 43. Thereby, a sufficiently large magnification factor can be achieved.

In one embodiment, the mirror 42 and the lens 43 are part of a transparent element and are located at the outer surfaces of the element. In an alternative embodiment, the mirror 42 and the lens 43 are separate elements.

In a preferred embodiment, the magnifying lens 43 is aspheric. By this means, the image quality can be improved. The lens 43 may also be constructed as a toric lens.

Usually, a user will look into the window 41 such that his/her line of sight corresponds to the normal direction $n_1$ of the window 41. Due to the fact that the window 41 is inclined against the outer surface of the dose dial element 30 at the indication position 32, the user will not frontally look at the indication position 32 of the dose dial element 30. In other words, the normal direction $n_1$ of the window 41 is not parallel but inclined to the normal direction $n_2$ of the outer surface of the dose dial element 30 at the indication position 32. In this embodiment, the magnifying device 4 does not enlarge the thickness of the medication delivery device 1 in a direction along the line of sight. Accordingly, by reflecting the light beams 51 at the mirror 42 and thereby by redirecting the optical path of the light beams 51, the distance between the outer surface of the lens 43 and the central axis of the pen-type device can be kept small while a sufficient magnification factor can be achieved. Therefore, the outer appearance of the medication delivery device 1 is less voluminous.

For the purpose of comparison, a similar magnification factor may be accomplished if the window 41, where the lens 43 is located, is located such that the normal direction $n_1$ of the window 41 coincides with the normal direction $n_2$ of the surface of the dose dial element 30 at its indication position 32 and in a distance from the surface of the dose dial element 30 which corresponds to the length of the optical path length in FIG. 2. In this case, the mirror can be omitted and the light beams emitted from the indication position 32 directly propagate towards the lens 43. By such a design of the magnifying device 4, however, the thickness of the medication delivery device 1 along the line of sight may be increased to an unacceptable high extent.

Figure 3:
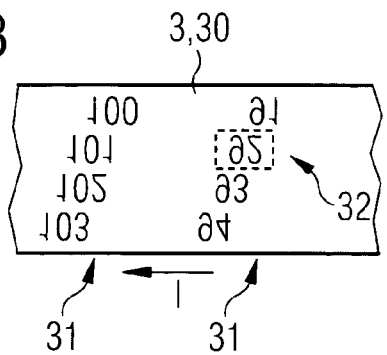
FIG. 3 is a top view of a dose dial element comprising a dosage scale.

FIG. 3 is a top view of a dose dial element 30 comprising a dosage scale 31. The dosage scale 31 consists of numerals 34 which are depicted in a mirror-inverted manner and are arranged helically on the surface of the dose dial element 30. At an indication position 31 of the dosage scale 31, the numeral 34 indicating the selected dose is present. The numerals 34 are depicted such that their magnified image 35 generated by the optical system 5 is visible through a window 41 oriented towards the left-hand side of the medication delivery device 1. Here, by the term "visible" it is meant, that the magnified image 35 appears in an upright, non-mirror-inverted orientation.

In an alternative embodiment of the medication delivery device 1, where the magnifying device 4 is oriented such that the selected dose can be viewed from the right hand side of the medication delivery device, the orientation of the numerals 34 has to be adapted.

Figure 5:
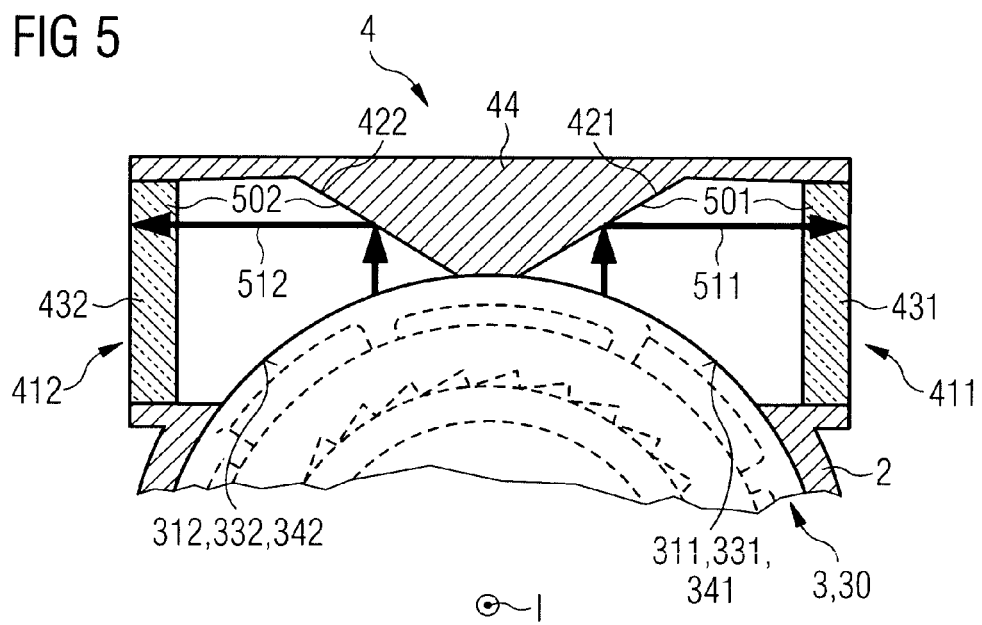
FIG. 5 is a cross-sectional view of the magnifying device of FIG. 3.

In FIG. 5, a medication delivery device 1 with a magnifying device 4 suitable for a right-handed or a left-handed person is shown. The magnifying device 4 comprises two windows 411, 412, whereof one 411 is oriented towards the left hand side of the medication delivery device 1 and the other one 412 is oriented to the right hand side. In a preferred embodiment, the size of the selected dose 33 can be viewed through only one 411 of the windows, while the other window 412 is masked. By this means, the user can not be confused by the fact that the dose is simultaneously displayed in several windows 411 412. Preferably, the medication delivery device is adjusted to the user such that for a left-handed user the selected dose 33 is visible only through the window 411 oriented to the right hand side of the medication delivery device 1 and for a right-handed user the selected dose 33 is visible only through the window 412 oriented to the left hand side of the medication delivery device 1.

In a preferred embodiment, after the construction of the medication delivery device 1, the selected dose 33 is visible through both windows 411, 412. A separate masking element is delivered together with the medication delivery device 1. Preferably, one of the windows 411, 412 is masked when the medication delivery device is handed over to the user. If the user is right-handed, the window 412 directed to the right hand side of the medication delivery device 1 should be masked. Accordingly, if the user is left-handed, the window 411 directed to the left hand side of the medication delivery device 1 should be masked. Alternatively, the medication delivery device 1 and the separate masking element are handed over to the user and the user attaches the masking element to one of the windows 411, 412.

Figure 4:
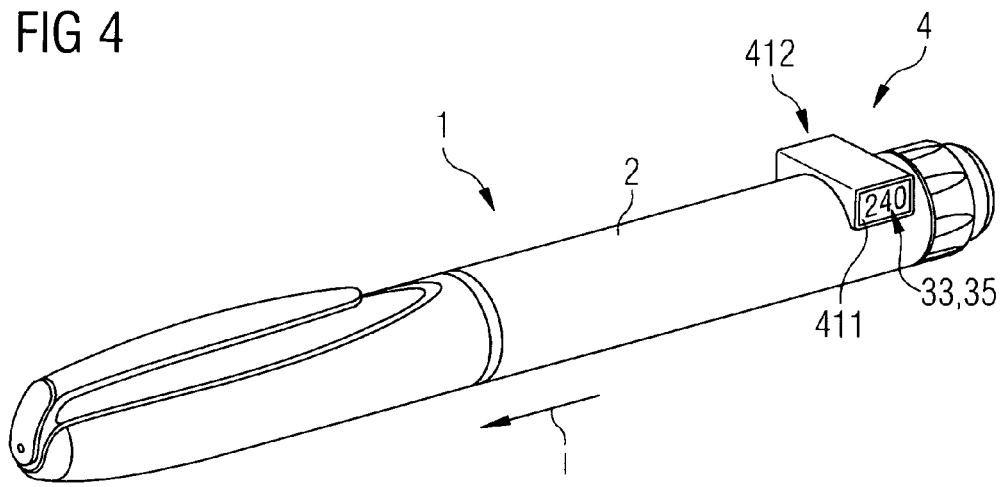
FIG. 4 is a perspective view of a medication delivery device comprising two magnifying devices.

FIG. 5 is a cross-sectional view of the magnifying device according to FIG. 4. In the casing 4, two optical systems 501, 502 are disposed. Each of the optical systems 501, 502 comprises a mirror 421, 422 and a magnifying lens 431, 432. The magnifying device 4 is located over two indication positions 321, 322 of two dosage scales 311, 312. At both indication positions 321, 322, a part of the dosage scale 311, 312 is present which indicates the selected dose 33. The magnifying device 4 is positioned such over the indication positions 321, 331 that light beams 511 emitted from one indication position 321 is reflected by the mirror 421 towards the lens 431. Thus, the size of the selected dose 33 can be viewed through the window 411 oriented towards the left hand side of the medication delivery device. Light beams 512 emitted from the second indication position 332 hit the mirror 422 and are reflected towards the second lens 432. Thus, the size of the selected dose 33 is visible through the window 412 oriented towards the right hand side of the medication delivery device.

Figure 6:
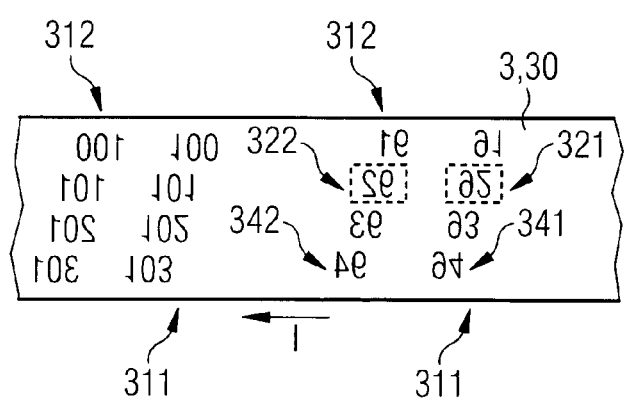
FIG. 6 is a top view of a dosage scale comprising two dosage scales.

FIG. 6 is a top view of a dose dial element 30 comprising two dosage scales 311, 312 which have an offset d in the longitudinal direction l of the medication delivery device. Accordingly, the indication positions 321, 322 have the same offset d. Both dosage scales 311, 312 comprise numerals 34 which are depicted in a mirror-inverted manner. The numerals 34 of the first dosage scale 311 are depicted such that their magnified images are readable through the window 411 oriented towards the left-hand side of the medication delivery device 1. Accordingly, the numerals 34 of the second dosage scale 312 are depicted such that their magnified images 35 are readable through the window 412 oriented towards the right-hand side of the medication delivery device 1.

Magnifying device 4 and medicament delivery device 1 may be designed to disable proper use, especially dose delivery, of the medicament delivery device by removing of the magnifying device 4.

The medicament delivery device 1 comprises at least two body parts, e.g. half shells or axially consecutive arranged body rings, wherein the magnifying device 4 forms a connection means for the at least two body parts of the medicament delivery device 1.

Additionally, the magnifying device 4 forms a support for parts of drive means of the medicament delivery device 1. Removal of the magnifying device 4 therefore leads to an interrupt of the force flux so that the load path is incomplete and dose setting and/or delivery is be inhibited.

A connection between the magnifying lens and the body and/or the drive means may be provided by laser welding or bonding.

Figure 7A:
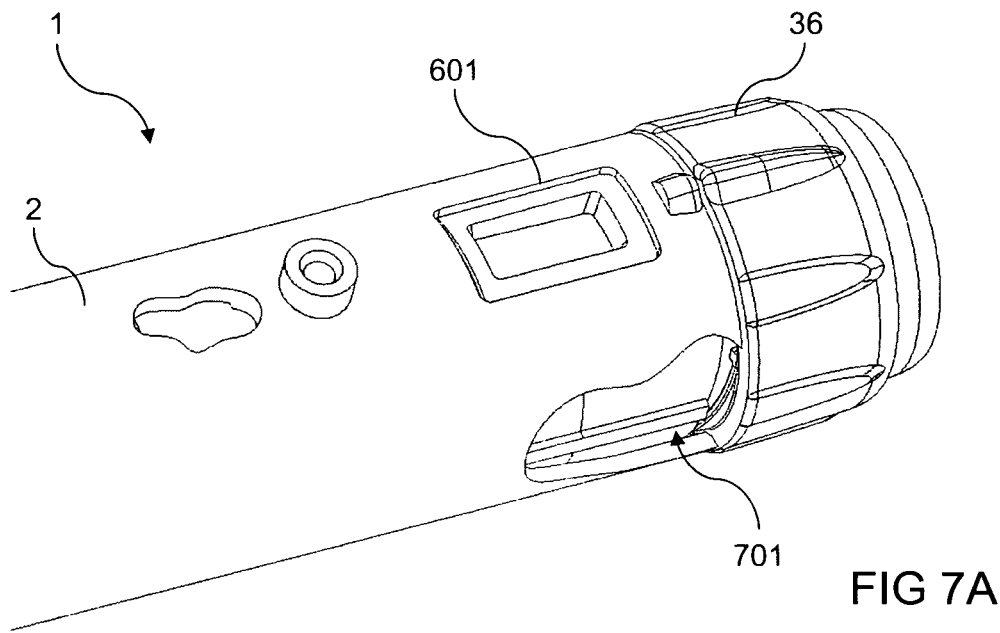
FIGS. 7A, 7B shows the medicament delivery device 1 after removal of The magnifying device 4.
Figure 7B:
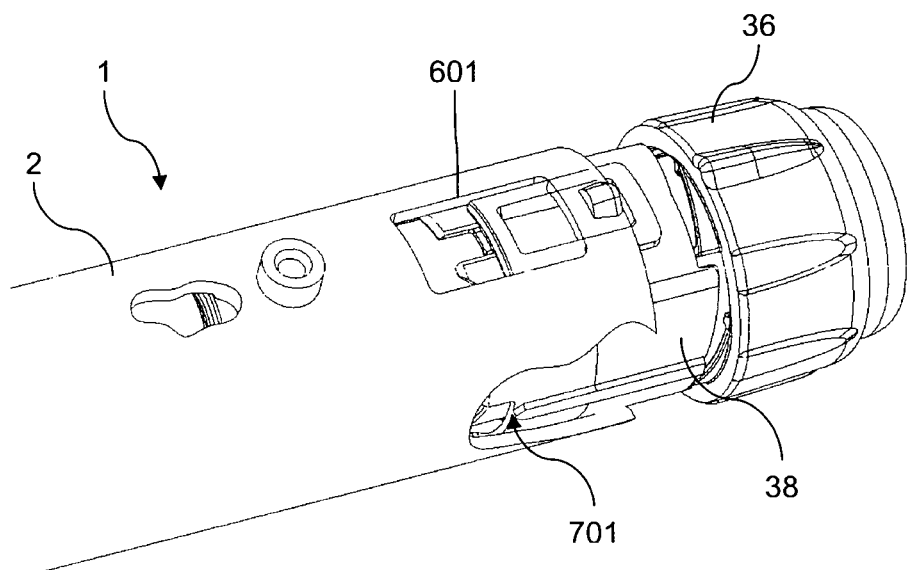

One exemplary embodiment of a medicament delivery device 1 designed to be self disabling after removal of the magnifying device 4 is shown in FIGS. 7A and 7B.

FIGS. 7A, 7B show the medicament delivery device 1 after removal of the magnifying device 4 (not shown). The removal of the magnifying device 4 leaves open a housing window 601 through which the optical path of the magnifying device 4 to its display window 41 is normally led.

Removal of the magnifying device 4 also leads to a partial destruction of the body 2 where parts of the body 2 will break away and leave open a hole 701. The part that broke away was part of the holding structure of a drive mechanism of the medicament delivery device 1, here a holding structure of a housing insert 38 through which the force flux is lead into the housing 2 while dose setting and injection, as can be seen in FIG. 7B. This leads to a release of the housing insert 38 which can no longer transfer any load into the body 2.

In the embodiment shown in FIGS. 7A and 7B parts of the drive mechanism are free to fall out of the body. In other embodiments the drive mechanism may not fall out of the body but due to the interruption of the load path, a dispense of a dose will be impossible.

Other implementations are within the scope of the following claims. Elements of different implementations may be combined to form implementations not specifically described herein.

Reference Signs 1 medication delivery device
2 housing
21 button
22 cap
23 front part of the housing
24 rear part of the housing
3 indicator element
30 dose dial element
300 indication
31, 311, 312 dosage scale
32, 321, 322 indication position
33 size of selected dose
34, 341, 342 mirror-inverted numeral
35 magnified image of indication
36 dose dial grip
38 housing insert 4, 401, 402 magnifying device
41, 411, 412 window
42, 421, 422 mirror
43, 431, 432 lens
44 casing
441 upper part of casing
442 lower part of casing
5, 501, 502 optical system
51, 511, 512 light beam
601 housing window
701 hole
d offset
l longitudinal direction

What is claimed is:

1. A medication delivery device comprising:
an indicator element having indications,
a magnifying device located over an indication position of the indicator element,
wherein the magnifying device comprises an optical system comprising a magnifying lens, and wherein the optical system is constructed such that the optical path length between the indication position and the magnifying lens is enlarged in comparison to a direct geometrical distance between the indication position and the magnifying lens.

2. The medication delivery device according to claim 1, wherein the optical system comprises a mirror that is suitable for reflecting light beams emitted from the indication position of the indicator element towards the magnifying lens.

3. The medication delivery device according to claim 1, wherein the magnifying device comprises a window through which a magnified image of an indication of the indicator element is visible.

4. The medication delivery device according to claim 3, wherein the window is inclined against an outer surface of the indicator element at its indication position.

5. The medication delivery device according to claim 4, wherein the magnifying device comprises two windows, and wherein one of the windows is suitable for making a magnified image of an indication visible from a left hand side of the medication delivery device and another one of the windows is suitable for making a magnified image of an indication visible from the right hand side of the medication delivery device.

6. The medication delivery device according to claim 5, having a longitudinal direction and
wherein the indicator element comprises two indication positions having an offset-in the longitudinal direction of the medication delivery device.

7. The medication delivery device according to claim 6, wherein a magnified image of an indication is visible through one window and wherein the other window is masked.

8. The medication delivery device according to claim 1, wherein the magnifying device is mounted such that removal of the magnifying device from the medicament delivery device disables use of the medicament delivery device.

9. The medicament delivery device according to claim 8, wherein the medicament delivery device comprises at least two body parts, wherein the magnifying device forms a connection means for the at least two body parts of the medicament delivery device.

10. The medicament delivery device according to claim 8, wherein the magnifying device forms a support for drive means of the medicament delivery device.

11. The medication delivery device according to claim 1 containing insulin.

* * * * *